(12) United States Patent
Piotrowski

(10) Patent No.: US 9,788,550 B2
(45) Date of Patent: Oct. 17, 2017

(54) DEODORIZER

(71) Applicant: Mary Piotrowski, Putnam Valley, NY (US)

(72) Inventor: Mary Piotrowski, Putnam Valley, NY (US)

(73) Assignee: Godors LLC, Sarasota, FL (US)

( * ) Notice: Subject to any disclaimer, the term of this patent is extended or adjusted under 35 U.S.C. 154(b) by 226 days.

(21) Appl. No.: 14/503,929

(22) Filed: Oct. 1, 2014

(65) Prior Publication Data

US 2015/0093352 A1 Apr. 2, 2015

Related U.S. Application Data

(60) Provisional application No. 61/885,203, filed on Oct. 1, 2013.

(51) Int. Cl.

| | |
|---|---|
| *A01N 61/00* | (2006.01) |
| *A61L 9/013* | (2006.01) |
| *C11D 3/00* | (2006.01) |
| *C11D 3/20* | (2006.01) |
| *C11D 3/48* | (2006.01) |
| *C11D 3/50* | (2006.01) |
| *A61L 2/18* | (2006.01) |
| *A61L 2/22* | (2006.01) |
| *A61L 9/14* | (2006.01) |

(52) U.S. Cl.
CPC ............ *A01N 61/00* (2013.01); *A61L 9/013* (2013.01); *C11D 3/0068* (2013.01); *C11D 3/2003* (2013.01); *C11D 3/48* (2013.01); *C11D 3/50* (2013.01); *A61L 2/18* (2013.01); *A61L 2/22* (2013.01); *A61L 9/14* (2013.01)

(58) Field of Classification Search
None
See application file for complete search history.

(56) References Cited

U.S. PATENT DOCUMENTS

| | | | |
|---|---|---|---|
| 2009/0092571 A1 | 4/2009 | Hirano et al. | |
| 2010/0101605 A1 | 4/2010 | Saint Victor | |
| 2011/0274643 A1 | 11/2011 | Yontz | |
| 2012/0009284 A1* | 1/2012 | Barnhill, Jr. ........... | A01N 31/02 424/747 |
| 2012/0164097 A1 | 6/2012 | Huchel et al. | |

FOREIGN PATENT DOCUMENTS

| | | |
|---|---|---|
| EP | 1 195 099 A2 | 4/2002 |
| JP | 2002 097302 A | 4/2002 |
| WO | 00/01423 A1 | 1/2000 |
| WO | 2011/143254 A2 | 11/2011 |

OTHER PUBLICATIONS

International Search Report and Written Opinion dated Jan. 7, 2015.

* cited by examiner

*Primary Examiner* — David J Blanchard
*Assistant Examiner* — Garen Gotfredson
(74) *Attorney, Agent, or Firm* — Dilworth & Barrese, LLP

(57) ABSTRACT

A deodorizer is provided herein which includes a fragrance containing a bubble gum flavor and cinnamaldehyde, a surfactant, a fungicide and bactericide in an alcohol/water solution. Also provided are methods of preparing and applying the deodorizer.

14 Claims, No Drawings

DEODORIZER

This application claims priority to U.S. Provisional Patent Application No. 61/885,203 filed Oct. 1, 2013, the entire content of which is incorporated herein by reference.

BACKGROUND

1. Field of the Invention

The present invention relates to a deodorizer and particularly a liquid deodorizer which can be applied, e.g., sprayed, onto malodorous articles such as athletic gear or clothing to neutralize offensive odors.

2. Background of the Art

Various agents for masking offensive odors are known. However, many of them do not work especially well on particularly malodorous articles, such as athletic gear or clothing which after use is typically moist with body sweat and offensive body odors. Provided herein is a formulation which neutralizes the offensive odors on such malodorous articles and leaves a pleasant after scent.

SUMMARY

A deodorizer is provided herein which includes a fragrance containing a bubble gum flavor, a surfactant, a fungicide and/or bactericide in an alcohol/water solution. Also provided herein are methods of preparing and applying the deodorizer.

DETAILED DESCRIPTION OF PREFERRED EMBODIMENT(S)

Other than in the working examples or where otherwise indicated, all numbers expressing amounts of materials, reaction conditions, time durations, quantified properties of materials, and so forth, stated in the specification and claims are to be understood as being modified in all instances by the term "about."

It will also be understood that any y numerical range recited herein is intended to include all sub-ranges within that range.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

Composition percentages are by volume at ambient temperature unless otherwise specified.

In one embodiment the deodorizer formulation of the present invention comprises a fragrance mixed with a surfactant, alcohol and water to which a fungicide such as, e.g., tea tree oil, and/or a bactericide such as, e.g., olive leaf extract, is added. The formulation is prepared in accordance with a method described below.

In an embodiment, the fragrance includes at least one bubble gum flavor. In a preferred embodiment, the fragrance is a liquid containing a bubble gum flavor and containing cinnamaldehyde in amounts, generally, of from about 0.1% to about 5% of the fragrance. Fragrances suitable for use in the disclosed deodorizer are commercially available from Value Fragrance and Flavors Co. of Goshen N.Y. 10924 under the designation M-0726 which is a bubble gum flavor liquid fragrance containing cinnamaldehyde or from Aquaverde, LLC, of Kearny, N.J. 07032 under the designation AQUA ODOR-B which is a bubble gum flavor liquid fragrance.

Surfactants suitable for use in the present deodorizer include any of the generally known and commercially available surfactants, such as cationic, anionic or non-ionic surfactants. Typical cationic surfactants include quaternary ammonium salts, amines with amide linkages, polyoxyethylene amines and 2-alkyl-1-hydroxyethyl-2-imidazolines. Typical anionic surfactants include carboxylates, sulfonates, alkylbenzenesulfonates, naphtalenesulfonates, olefin sulfonates and alkylsulphates. Suitable non-ionic surfactants include polyalkyleneoxides such as ethoxylated non-ionic surfactants, propoxylated non-ionic surfactants or ethoxylated/propoxylated copolymer non-ionic surfactants. For example, some suitable ethoxylated and/or propoxylated non-ionic surfactants are available from Dow Chemical Co. under the designations Tergitol™ NP-9 (nonylphenol ethoxylates) or Tergitol™ 15-S series (secondary alcohol ethoxylates). Some ethoxylated/propoxylated copolymer non-ionic surfactants include polyoxypropylene/polyoxyethylene/polyoxypropylene (PO/EO/PE) and or polyoxyethylene/polyoxypropylene/polyoxyethylene (EO/PO/EO). An example of an ethoxylated/propoxylated copolymer non-ionic surfactant is Tergent® SLF-18 which is commercially available. Other non-ionic surfactants that are also suitable for the present deodorizer include other polyethylene glycols, such as, polyethylene glycol isocetyl ether; ethanolamides, such as, coamide DEA and cocamide MEA; fatty alcohols, such as decyl alcohol, cetostearyl alcohol, stearyl alcohol, oleyl alcohol; fatty esters, such as, sorbitan monostearate and sorbitan tristearate; glycosides, such as, decyl glucoside, lauryl glucoside and octyl glucoside; mono glycerides such as monolaurin; poloxamers, such as, poloxamer 407; polysorbates, such as, polysorbate 20, polysorbate 40 polysorbate 60 and polysorbate 80. For the purposes of the present disclosure, non-ionic surfactants are preferred.

Alcohols suitable for use in the deodorizer disclosed herein include primary, secondary or tertiary alcohols. These alcohols can be linear or branched. In one embodiment, the alcohol has from 1 to 12 carbon atoms. In a specific embodiment, the alcohol includes at least one of ethyl alcohol, propyl alcohol or isopropyl alcohol. In one embodiment, the alcohol is a commercially available formulation containing from 70% to 99% alcohol. In another embodiment, 99% isopropyl alcohol is preferred.

In one embodiment, the water suitable for use in the deodorizer disclosed herein is preferably free of chloride and fluoride and can be, for example, distilled water, well water, spring water, filtered water, and the like.

Fungicides suitable for use in the disclosed deodorizer include, for example, tea tree oil, cinnamon oil, citronella oil, jojoba oil, neem oil, oregano oil, rosemary oil, monocerin. In an embodiment of the deodorizer disclosed herein, the deodorizer comprises a fungicide in amounts of from about 0.01% to about 2.5% and more specifically from about 0.01% to about 0.12%. In a specific embodiment, the fungicide is a tea tree oil. Typically, tea tree oils include at least one of a monoterpene, monoterpenic alcohol, a sesquiterpene, a sesquiterpene alcohol, or aromatic compounds. In one embodiment, the deodorizer comprises tea tree oil in amounts of from about 0.01% to about 2.5% and in more specific embodiments the tea tree oil is from about 0.01% to about 0.12% of the deodorizer fluid.

Some embodiments of the deodorizer include at least one bactericide. In some embodiments, the fungicides disclosed above also have bactericide functionality. In a specific embodiment, the bactericide used in the deodorizer is present in amounts of from about 0.03% to about 0.35%. Although it is contemplated within the scope of the present disclosure that bactericides known to those of ordinary skill in the art may be used in the disclosed deodorized, some specific bactericides suitable for inclusion in the disclosed deodorizer include olive leaf extract; argan oil; extracts from tree barks such as the Mouton bark; limonoid and bioflavonoids extractable from the peel, seeds, pulp and skin of citrus fruits; Cetylpyridinium chloride salicylaldehyde; triclosan; acyclic sesquiterpene alcohols such as farnesol; eucalyptol; menthol; methylsalicylate; thymol; and mixtures thereof. In a specific embodiment, the bactericide comprises at least one of an olive leaf extract. Typical extracts from olive leaf include, for example, at least one of oleuropein and hydroxytyrosol, as well as several other polyphenols and flavonoids, including oleocanthal. Although the extracts can be in powder or liquid form and either would be suitable for inclusion in the present deodorizer, in a preferred embodiment, the extract is in liquid form. For example, the extract may form part of a solution with water or an alcohol such as for example, ethyl alcohol, propyl alcohol or iso-propyl alcohol. In a specific embodiment, the olive leaf extract used in the liquid form of the olive leaf extract is present in the liquid in amounts of from about 0.10% to about 0.50% and in more specific embodiments is in amounts of from about 0.2% to about 0.4% and most specifically about 0.39%. In some embodiments the liquid for the olive leaf extract is water and in specific embodiments the water can be free of chloride a td fluoride and can be, for example, distilled water, well water, spring water, filtered water, and the like.

Both tea tree oil and olive leaf extract are commercially available from various suppliers. In a specific embodiment, the deodorizer fluid comprises one part of the tea tree oil solution and three parts of the olive leaf extract solution.

The term "extract" as used herein means an extract in a solvent available by extracting the plant in a proper solvent at normal temperature or under heating, or extracting the plant by using an extraction tool such as a Soxhlet extractor; or a diluted solution, concentrate or dry powder of those extracts. Solvents suitable for extraction are known to those of skill in the art and are readily available.

It has been found that the deodorizer disclosed herein can, in one embodiment, be prepared by first mixing the fragrance and the surfactant before incorporating the alcohol and water to form an initial fragrance solution. In a specific embodiment of the deodorizer the initial fragrance solution is formed at ambient temperature. While not wishing to be bound by any specific theory, it is believed that mixing at ambient temperature reduces the risk of fumes and reduces the loss of components of the initial fragrance solution.

In one embodiment, preparation of the deodorizer comprises preparation of an initial fragrance solution. An initial fragrance solution is provided containing the following components:
  Fragrance from about 5% to about 15%
  Alcohol from about 1% to about 15%
  Surfactant from about 10% to about 20%
  Water from about 60% to about 85%
In a more specific embodiment, the initial fragrance solution contains the following percentage composition:
  about 10% fragrance
  about 3% alcohol (e.g., isopropyl alcohol)
  about 12% surfactant
  about 75% water In an embodiment of the disclosed method for making the deodorizer, the initial fragrance solution is formed by first adding the fragrant to the surfactant and then the alcohol and water are added alternately with sufficient stirring to prevent separation of the components into separate layers.

The method further includes steps of including the fungicide and bactericide into the deodorizer. In one embodiment, to one part of the initial fragrance solution, as prepared above, is added one part of alcohol/tea tree oil solution and three parts of water/olive leaf extract solution. The alcohol/tea tree oil solution preferably contains about 0.10% to about 0.50%, more preferably about 0.2% to about 0.4%, and most specifically about 0.39%, tea tree oil in isopropyl alcohol. The water/olive leaf extract solution preferably contains 0.10% to about 0.50%, and more preferably about 0.39% olive leaf extract in water. The alcohol/tea tree oil solution and the water/olive leaf extract solution are added to the initial fragrance solution in an alternating fashion with sufficient stirring to prevent separation of the components into separate layers. The result is a clear deodorizer liquid. In one embodiment, the deodorizer is a liquid of light yellow color.

In a preferred embodiment the final deodorizer is a liquid (i.e., solution or emulsion). In one embodiment, the final deodorizer liquid is suitable for application by at least one of spraying, coating or wiping onto a substrate surface such as the equipment or clothes described herein. It is contemplated that in certain specific embodiments, the deodorizer is a liquid that includes the following components and composition percentages:

| Component | Range | Example | |
|---|---|---|---|
| Fragrance | about 0.50-about. 5.0% | 2.00% | (liquid containing bubble gum flavor and cinnamaldehyde M-0726) |
| Alcohol | about 15.00-about 30.0% | 20.52% | (Isopropyl alcohol) |
| Surfactant | about 1.00-about 5.0% | 2.40% | (Tergitol ™ NP-9) |
| Water | about 60.00-about 80.0% | 74.77% | (chlorine free water) |
| Fungicide | about 0.01-about 0.12% | 0.08% | (Tea tree oil) |
| Bactericide | about 0.03-about 0.35% | 0.23% | (Olive leaf extract) |
| Total | | 100.00% | |

The percentages may be varied where appropriate for the purposes described herein. The fragrance, surfactant, alcohol, water, fungicide and bactericide can be selected from those disclosed herein.

The deodorizer can be used on any items which become malodorous because of body sweat or other body odors, but is ideally suitable for use on athletic equipment or clothing such as sneakers shoes, shirts, socks, doves, helmets, pants, pads, and guards typically worn in activities where unwanted odors are generated. For example the equipment of clothing can be used in activities of physical exertion such as running, hockey, lacrosse, fencing, football, baseball, soccer and other sports such as hiking, backpacking, cycling, etc. The deodorizer can be used on fabrics or hard surfaces such as plastic, wood, or metal. The deodorizer is quick drying, safe for human use and is biodegradable. When applied, the deodorizer has an initial bubble gum scent followed by a pleasant cinnamon like scent.

In certain embodiments, the deodorizer is applied before or after use of the equipment or clothing in either a prophylactic manner or curative manner such that the formation of the malodor is at least reduced or if already present is at least reduced. In some embodiments the malodor is either completely prevented or is completely eliminated.

In one embodiment of the use, the deodorizer is sprayed and/or wiped onto the equipment surfaces. Items such as gloves are preferably sprayed both on interior and exterior surfaces. Helmets are preferably treated by applying the deodorizer spray onto a paper towel and then wiping the helmet interior pads and external plastic surfaces with the paper towel. After about ten minutes the treated surfaces can then be wiped with a paper towel dampened with water. In a preferred method, the malodorous equipment and/or clothing is contained in an athletic carrying bag, sprayed with the deodorizer, and the bag thereafter zipped or otherwise closed.

The deodorizer of the invention can be stored in any suitable glass or plastic container. For purposes of application the deodorizer is preferably dispensed from, for example a pump-spray type bottle or plastic container. Pressurized spray cans may also be used for dispensing the deodorizer of the invention.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A deodorizer consisting of:
   a) a fragrance which contains a bubble gum flavor and cinnamaldehyde;
   b) a non-ionic surfactant;
   c) alcohol;
   d) water;
   e) a fungicide; and
   f) a bactericide.

2. The deodorizer of claim 1, wherein the cinnamaldehyde is present in an amount of from about 0.1% to about 5% of the fragrance.

3. The deodorizer of claim 1 wherein the alcohol is isopropyl alcohol.

4. The deodorizer of claim 1 wherein the fungicide is tea tree oil.

5. The deodorizer of claim 1 wherein the bactericide is olive leaf extract.

6. A deodorizer consisting of:
   about 0.50-about 5.0% by volume of a fragrance which contains cinnamaldehyde;
   about 15.00-about 30.0% by volume of isopropyl alcohol; about 1.00-about 5.0% by volume of a nonionic surfactant; about 60.00-about 80.0% by volume water free of chloride and fluoride;
   about 0.01-about 0.12% by volume tea tree oil; and
   about 0.03-about 0.35% olive leaf extract.

7. The deodorizer of claim 6 consisting of:
   about 2.00% by volume of the fragrance;
   about 20.52% by volume of the isopropyl alcohol;
   about 2.40% by volume of the non-ionic surfactant;
   about 74.77% by volume of the chloride and fluoride free water;
   about 0.08% by volume of the tea tree oil; and
   about 0.23% by volume of the olive leaf extract.

8. A method of deodorizing a malodorous object by applying to the malodorous object the deodorizer of claim 1.

9. The method of claim 8 wherein the step of applying the deodorizer comprises spraying the deodorizer onto an exterior and/or interior surface of the object.

10. The method of claim 9 wherein the malodorous object comprises moist or dry athletic equipment.

11. The method of claim 10 wherein the athletic equipment comprises one or more of sneakers, shoes, shirts, socks, gloves, helmets, pants, pads, or guards.

12. The method of claim 11 wherein the athletic equipment is for hockey, lacrosse, fencing, football, baseball, soccer, hiking, backpacking, or cycling.

13. The deodorizer of claim 1 wherein ingredients (a)-(f) are incorporated in proportions to release an initial bubble gum scent followed by a cinnamon-like scent upon application.

14. The deodorizer of claim 1 in the form of a spray.

* * * * *